US009518933B2

(12) United States Patent
Chatterton et al.

(10) Patent No.: US 9,518,933 B2
(45) Date of Patent: Dec. 13, 2016

(54) OPTO-ELECTRONIC INSPECTION QUALITY ASSURANCE SYSTEM FOR FLUID DISPENSING VALVES

(71) Applicant: Entegris, Inc., Billerica, MA (US)

(72) Inventors: Thomas E. Chatterton, Round Rock, TX (US); Sebum Cheon, New Milford, CT (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

(21) Appl. No.: 14/433,363

(22) PCT Filed: Oct. 12, 2013

(86) PCT No.: PCT/US2013/064732
§ 371 (c)(1),
(2) Date: Apr. 2, 2015

(87) PCT Pub. No.: WO2014/059395
PCT Pub. Date: Apr. 17, 2014

(65) Prior Publication Data
US 2015/0276619 A1    Oct. 1, 2015

Related U.S. Application Data

(60) Provisional application No. 61/713,492, filed on Oct. 13, 2012.

(51) Int. Cl.
| G01N 21/00 | (2006.01) |
| G01N 21/95 | (2006.01) |
| G01B 11/00 | (2006.01) |
| G01N 21/88 | (2006.01) |
| G01B 13/00 | (2006.01) |
| G01B 11/30 | (2006.01) |

(52) U.S. Cl.
CPC ............... *G01N 21/95* (2013.01); *G01B 11/00* (2013.01); *G01B 11/303* (2013.01); *G01B 13/00* (2013.01); *G01N 21/8806* (2013.01); *G01N 2201/062* (2013.01); *G01N 2201/06113* (2013.01)

(58) Field of Classification Search
CPC combination set(s) only.
See application file for complete search history.

(56) References Cited

U.S. PATENT DOCUMENTS

| 3,680,966 A * | 8/1972 | Cofek ................ G01B 11/12 250/223 B |
| 4,692,943 A | 9/1987 | Pietzsch et al. |
| 5,279,729 A | 1/1994 | Tone et al. |
| 5,389,544 A * | 2/1995 | Sugata ............... G01N 15/1459 250/458.1 |
| 5,680,473 A | 10/1997 | Kanzaka et al. |
| 2004/0218807 A1 | 11/2004 | Alumot et al. |
| 2008/0186481 A1 | 8/2008 | Chen |

* cited by examiner

*Primary Examiner* — Tri T Ton

(57) ABSTRACT

An optoelectronic inspection system useful for quality assurance determinations of fluid dispensing valves, e.g., as installed on fluid storage and dispensing vessels, and associated methodology and non-transitory computer readable media storing machine-executable instructions for such quality assurance determinations, are described. The optoelectronic inspection is applicable to flow control valves used on fluid storage and dispensing packages including physical adsorbent-based and/or pressure-regulated vessels, such as are used for supply of processing fluids used in the manufacture of semiconductor products, flat panel displays, and solar panels.

20 Claims, 14 Drawing Sheets

OPTO-ELECTRONIC INSPECTION QUALITY ASSURANCE SYSTEM FOR FLUID DISPENSING VALVES

CROSS-REFERENCE TO RELATED APPLICATIONS

This application is a U.S. national phase under the provisions of 35 U.S.C. §371 of International Patent Application No. PCT/US13/64732 filed Oct. 12, 2013 in the names of Thomas E. Chatterton, et al. for OPTOELECTRONIC INSPECTION QUALITY ASSURANCE SYSTEM FOR FLUID DISPENSING VALVES, which in turn claims the benefit of priority under 35 USC 119 of U.S. Provisional Patent Application No. 61/713,492 filed Oct. 13, 2012 in the name of Thomas Chatterton, et al. for "OPTOELECTRONIC INSPECTION QUALITY ASSURANCE SYSTEM FOR FLUID DISPENSING VALVES". The disclosures of such International Patent Application No. PCT/US13/64732 and U.S. Provisional Patent Application No. 61/713,492 are hereby incorporated herein by reference in their respective entireties, for all purposes.

FIELD

The present invention relates to an optoelectronic inspection system useful for quality assurance determinations of fluid dispensing valves, e.g., as installed on fluid storage and dispensing vessels, as well as to associated methodology and non-transitory computer readable media storing machine-executable instructions for such quality assurance determinations.

DESCRIPTION OF THE RELATED ART

In the use of fluid storage and dispensing packages comprising fluid containment vessels and valve head assemblies, in which the valve head assembly includes a flow control valve, it is imperative that the flow control valve be operable between fully open and fully closed states so that the fluid dispensing operation is carried out in an effective and efficient manner.

In such flow control valves, the valve element that is translatable between the fully open and fully closed states must effect fluid tight sealing in the closed condition, and afford precise modulation of fluid flow when the valve is at least partially open, dependent on the specific position of the valve element in the valve chamber. This is particularly critical in applications such as manufacturing of semiconductor products, flat-panel displays, and solar panels, in which fluid being dispensed may be of toxic or hazardous character, with high cost per unit volume, and fluid utilization requirements for downstream process equipment that may include ultrahigh purity and/or critical concentration requirements for the dispensed fluid.

Flow control valves in such applications are typically submitted to quality assurance inspection at the time of initial fabrication of the fluid storage and dispensing packages containing same, as well as when the fluid package is returned in an empty condition to a fluid fill station or facility for refilling of the vessel with fresh fluid. Such quality assurance inspection typically involves manual, visual inspection, which is a time-consuming and costly activity.

SUMMARY

The present disclosure relates to an optoelectronic inspection system useful for quality assurance determinations of fluid dispensing valves, e.g., as installed on fluid storage and dispensing vessels, as well as to associated methodology and non-transitory computable readable media storing machine-executable instructions for such quality assurance determinations.

In one aspect, the disclosure relates to an optoelectronic inspection system for determining acceptability of a valve structure, comprising:

an inspection station adapted to position the valve structure for optoelectronic imaging;

a light source arranged to impinge light on the valve structure;

a camera/lens assembly arranged to receive light resulting from interaction of the valve structure and light impinged on the valve structure from the light source, and to responsively generate an optoelectronic imaging output;

a central processing unit arranged to receive the optoelectronic imaging output from the camera/lens assembly and to responsively generate an inspection output indicative of whether the valve structure satisfies predetermined acceptability criteria.

In another aspect, the disclosure relates to a method for determining acceptability of a valve structure, comprising:

impinging light from a light source on the valve structure to cause an interaction of the impinged light and the valve structure producing an imaging response;

optoelectronically generating an optoelectronic imaging output based on the imaging response; and electronically generating, via a central processing unit receiving and processing the optoelectronic imaging output, an inspection output indicative of whether the valve structure satisfies predetermined acceptability criteria.

In a further aspect, the disclosure relates to a non-transitory computer readable medium storing machine-executable instructions which when executed carry out a quality assurance determination of a fluid dispensing valve including valve structure on which light has been impinged to produce an imaging response optoelectronically converted to an optoelectronic imaging output, wherein said optoelectronic imaging output is processed to generate an inspection output indicative of whether the valve structure satisfies predetermined acceptability criteria.

Other aspects, features and embodiments of the disclosure will be more fully apparent from the ensuing description and appended claims.

DETAILED DESCRIPTION

Figure 1:
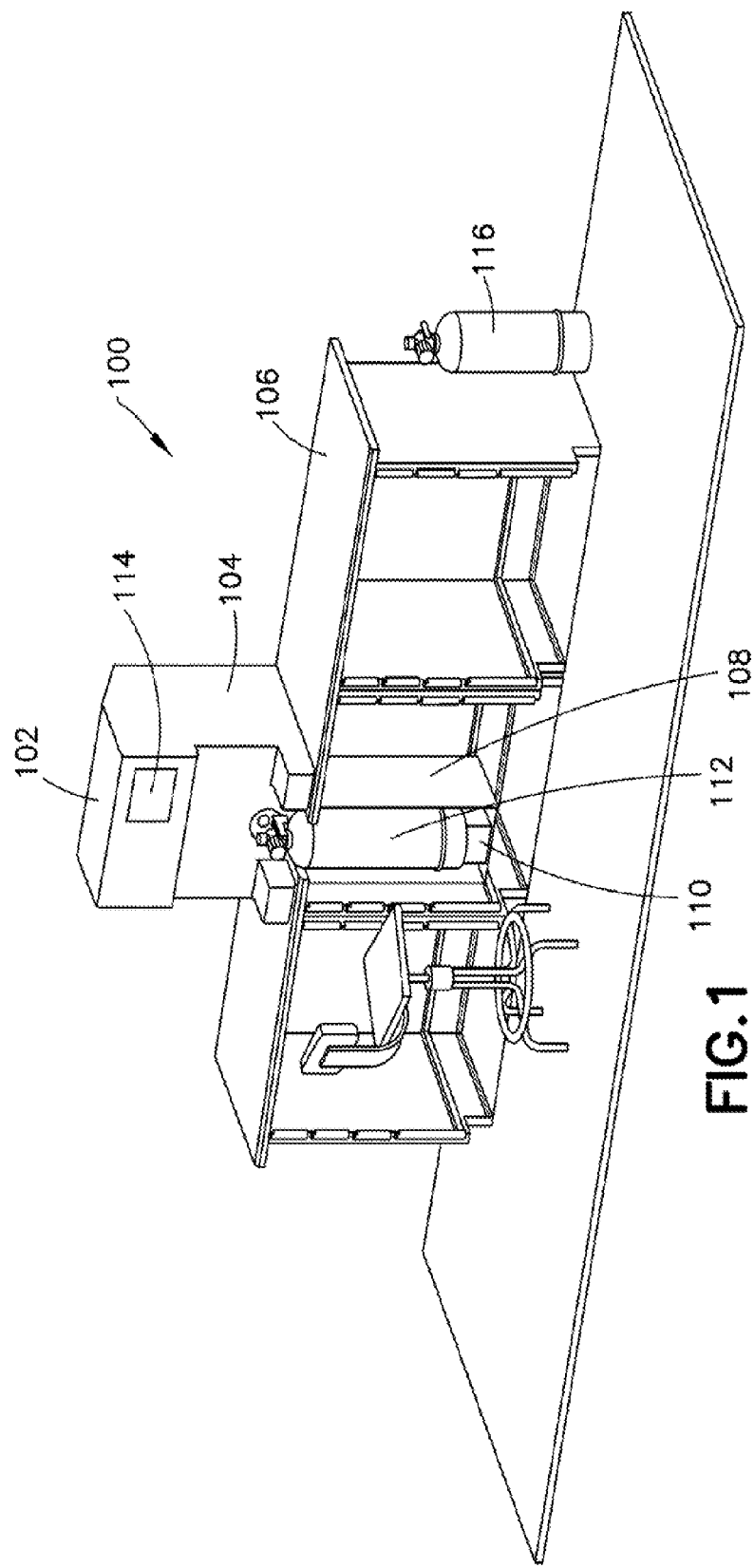
FIG. 1 is a schematic representation of an optoelectronic inspection system according to one embodiment of the present disclosure.

The present disclosure relates to an optoelectronic inspection system useful for quality assurance determinations of fluid dispensing valves, e.g., as installed on fluid storage and dispensing vessels, as well as to associated methodology and non-transitory computable readable media storing machine-executable instructions for such quality assurance determinations.

In one aspect, the disclosure relates to an optoelectronic inspection system for determining acceptability of a valve structure, comprising:

an inspection station adapted to position the valve structure for optoelectronic imaging;

a light source arranged to impinge light on the valve structure;

a camera/lens assembly arranged to receive light resulting from interaction of the valve structure and light impinged on the valve structure from the light source, and to responsively generate an optoelectronic imaging output;

a central processing unit arranged to receive the optoelectronic imaging output from the camera/lens assembly and to responsively generate an inspection output indicative of whether the valve structure satisfies predetermined acceptability criteria.

In such optoelectronic inspection system, the inspection station in one embodiment is adapted to position the valve structure for optoelectronic imaging, via a holder arranged to retain a fluid supply package including a valve head assembly comprising said valve structure in appropriate position for optoelectronic imaging.

The light source in the optoelectronic inspection system can be of any suitable type, and may for example comprise an illumination device selected from the group consisting of incandescent lamps, light emitting diodes, lasers, ultraviolet lamps, and infrared lamps. The light source may therefore be of a type emitting visible light, infrared radiation, ultraviolet radiation, or other suitable light output that when impinged on the valve structure enables a response signature to be produced that is correlative of the character, quality or condition of the valve structure.

The central processing unit in the optoelectronic inspection system can likewise be of any suitable type, and may for example comprise a processor generating a colorimetric inspection output indicative of whether the valve structure satisfies predetermined acceptability criteria. The colorimetric inspection output can be of any color or color combination that provides an appropriate inspection result. For example, the colorimetric inspection output can comprise a green color output when a valve structure satisfies the predetermined acceptability criteria, and a red color output when a valve structure does not satisfy the predetermined acceptability criteria.

The central processing unit of the optoelectronic inspection system may be of any appropriate type, and may for example comprise a non-transitory computer readable medium storing machine-executable instructions for determining acceptability of a valve structure. The central processing unit may comprise a non-transitory computer readable medium storing a database of criteria of acceptable valve structure. The central processing unit may be adapted to process the optoelectronic imaging output from the camera/lens assembly for determination of compatibility thereof with the criteria of acceptable valve structure in order to responsively generate the inspection output indicative of whether the valve structure satisfies the predetermined acceptability criteria.

In various embodiments, the optoelectronic inspection system further comprises a transporter apparatus adapted to move a fluid supply package including the valve structure being assessed, from the inspection station to one of multiple receiving areas dependent on extent of matching by a valve structure thereof to the predetermined acceptability criteria. The receiving areas may for example include a first area for receipt of fluid supply packages whose valve structure satisfies the predetermined acceptability criteria, and a second area for receipt of fluid supply packages whose valve structure does not satisfy the predetermined acceptability criteria. Optionally, the receiving areas may include a third area for receipt of fluid supply packages whose valve structure does not satisfy the predetermined acceptability criteria, but is within a predetermined sufficient proximity to the predetermined acceptability criteria so as to be reworkable to yield a reworked valve structure satisfying the predetermined acceptability criteria.

The disclosure in another aspect relates to a method for determining acceptability of a valve structure, comprising: impinging light from a light source on the valve structure to cause an interaction of the impinged light and the valve structure producing an imaging response;
optoelectronically generating an optoelectronic imaging output based on the imaging response; and
electronically generating, via a central processing unit receiving and processing the optoelectronic imaging output, an inspection output indicative of whether the valve structure satisfies predetermined acceptability criteria.

In such method, the valve structure can be a component of a valve head assembly of a fluid supply package. Alternatively, the valve structure may be internal valve chamber structure of a flow control valve per se.

The method may be carried out with any suitable light source, e.g., an illumination device selected from the group consisting of incandescent lamps, light emitting diodes, lasers, ultraviolet lamps, and infrared lamps. As discussed hereinabove, the light source utilized in the quality assurance determination of the present disclosure may emit visible light, infrared radiation, ultraviolet radiation, or any other suitable electromagnetic radiation.

The method may be carried out to produce an inspection output comprising a colorimetric inspection output indicative of whether the valve structure satisfies predetermined acceptability criteria, e.g., a colorimetric inspection output comprising a green color output when a valve structure satisfies the predetermined acceptability criteria, and a red color output when a valve structure does not satisfy the predetermined acceptability criteria.

The method may be conducted with the central processing unit comprising a non-transitory computer readable medium that stores machine-executable instructions for determining the acceptability of a valve structure. The central processing unit may comprise a non-transitory computer readable medium storing a database of criteria of acceptable valve structure. The central processing unit may be adapted to process the optoelectronic imaging output for determination of compatibility thereof with the criteria of acceptable valve structure in order to responsively generate the inspection output indicative of whether the valve structure satisfies predetermined acceptability criteria.

The method may further comprise, after generating the inspection output, mechanically moving a fluid supply package comprising the valve structure to one of multiple receiving areas dependent on extent of matching by a valve structure thereof to the predetermined acceptability criteria. The receiving areas, as previously described, may include a first area for receipt of fluid supply packages whose valve structure satisfies the predetermined acceptability criteria, and a second area for receipt of fluid supply packages whose valve structure does not satisfy the predetermined acceptability criteria, and optionally a third area for receipt of fluid supply packages whose valve structure does not satisfy the predetermined acceptability criteria, but is within a predetermined sufficient proximity to the predetermined acceptability criteria so as to be reworkable to yield a reworked valve structure satisfying the predetermined acceptability criteria.

In a further aspect, the disclosure relates to a non-transitory computer readable medium storing machine-executable instructions which when executed carry out a quality assurance determination of a fluid dispensing valve including valve structure on which light has been impinged to produce an imaging response optoelectronically converted to an optoelectronic imaging output, wherein the optoelectronic imaging output is processed to generate an inspection output indicative of whether the valve structure satisfies predetermined acceptability criteria.

The non-transitory computer readable medium may be constituted so that the processing of the optoelectronic imaging output comprises correlation thereof with fluid dispensing valve baseline information for a valve of a type being subjected to the quality assurance determination, from a database of fluid dispensing valve baseline information for multiple valve types.

The features, aspects, and embodiments of the disclosure will be further appreciated in the context of the ensuing description of the drawings of FIGS. 1-17.

FIG. 1 is a schematic representation of an optoelectronic inspection system 100 according to one embodiment of the present disclosure. The system includes an inspection assembly 102, comprising housing 104 and display screen 114, reposed on bench 106 to constitute an inspection station. The countertop of bench 106 has a cutout on a frontal portion thereof to accommodate positioning of the vessel of the fluid storage and dispensing package 112 so that the net and valve head assembly of the vessel extend upwardly above the surface of the countertop, with the vessel positioned on pedestal 110 mounted in the bracket 108 secured to the underside of the countertop. Also shown in FIG. 1 is a fluid storage and dispensing package 116 awaiting quality assurance testing by the inspection assembly 102.

It will be recognized that the inspection station shown in FIG. 1 involves manual placement of successive fluid storage and dispensing packages in the bracket 108 on pedestal 110 for quality assurance determination, followed by manual removal of the fluid package from the bracket to accommodate the next-successive fluid package to be subjected to the quality assurance operation.

Alternatively, the inspection station may be constructed, arranged and adapted for automated delivery and positioning of successive fluid packages in the bracket for quality assurance determination, and subsequent automated removal of the inspected fluid package from the bracket of the inspection station, and transport to a specific area dependent on the outcome of the quality assurance operation.

For example, the optoelectronic inspection system may further comprise a delivery and transport system that furnishes a fluid package to the inspection station, subjects the valve assembly of such fluid package to quality assurance determination, and then transports fluid packages satisfying quality assurance criteria to a first retention area, and transports fluid packages failing quality assurance criteria to a second retention area. Fluid packages in the second retention area then may be reworked, such as by removing the valve head assembly from the vessel of such package and replacing it with a replacement valve head assembly, subsequent which the fluid package is again submitted to quality assurance determination.

Figure 2:
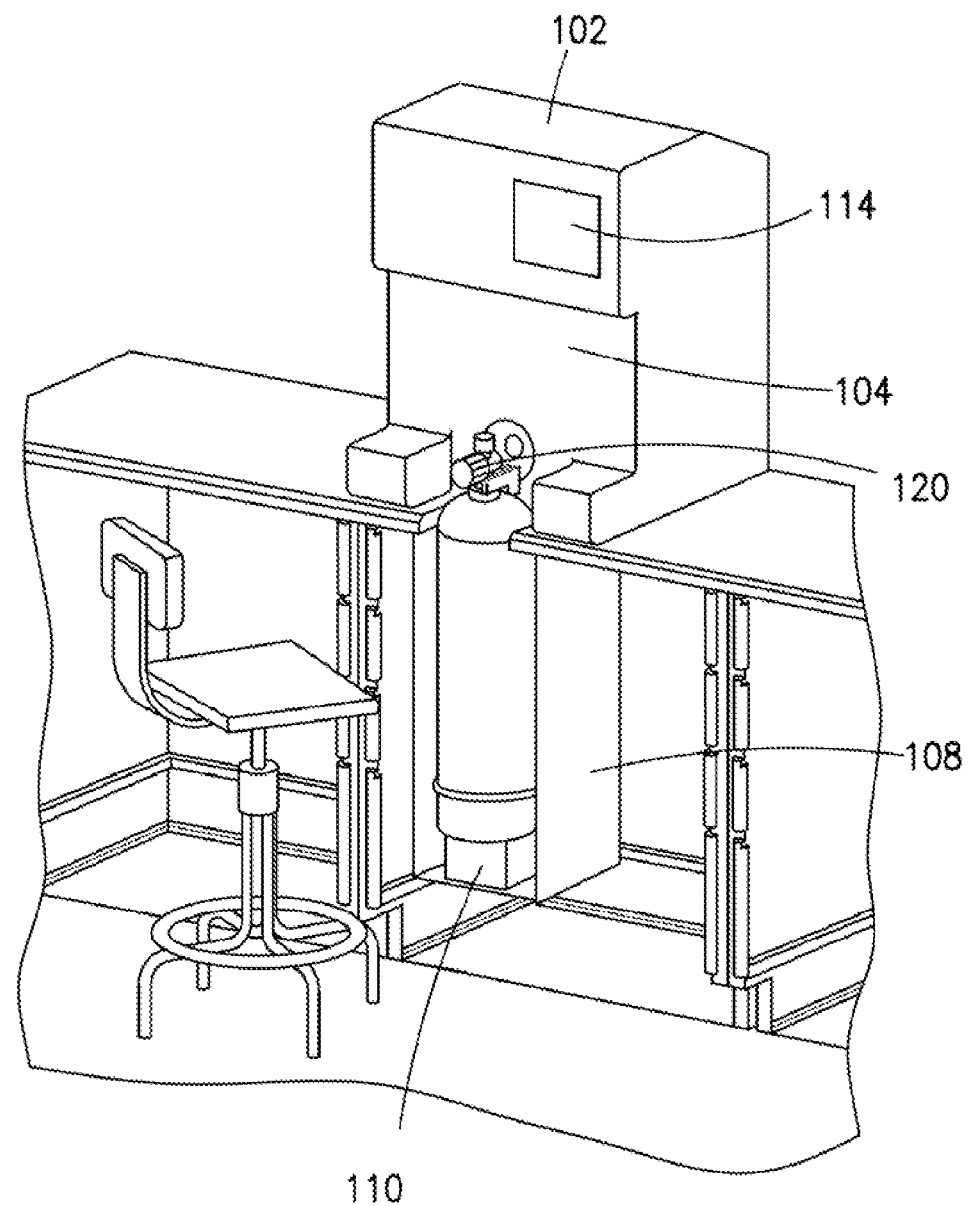
FIG. 2 is a close-up perspective view of the optoelectronic inspection system of FIG. 1.

FIG. 2 is a close-up perspective view of the optoelectronic inspection system of FIG. 1, showing the features thereof. As illustrated, the inspection assembly 102 comprises a housing 104 containing optical and electronic componentry, as hereinafter more fully described. The inspection assembly 102 includes a display 114, which may for example comprise a liquid crystal display or other visual output screen for display of data and/or results of the quality assurance determination. A fluid package is shown in the bracket 108, supported on pedestal 110, with the valve head assembly 120 of the fluid package being positioned by such arrangement for quality assurance determination.

Figure 3:
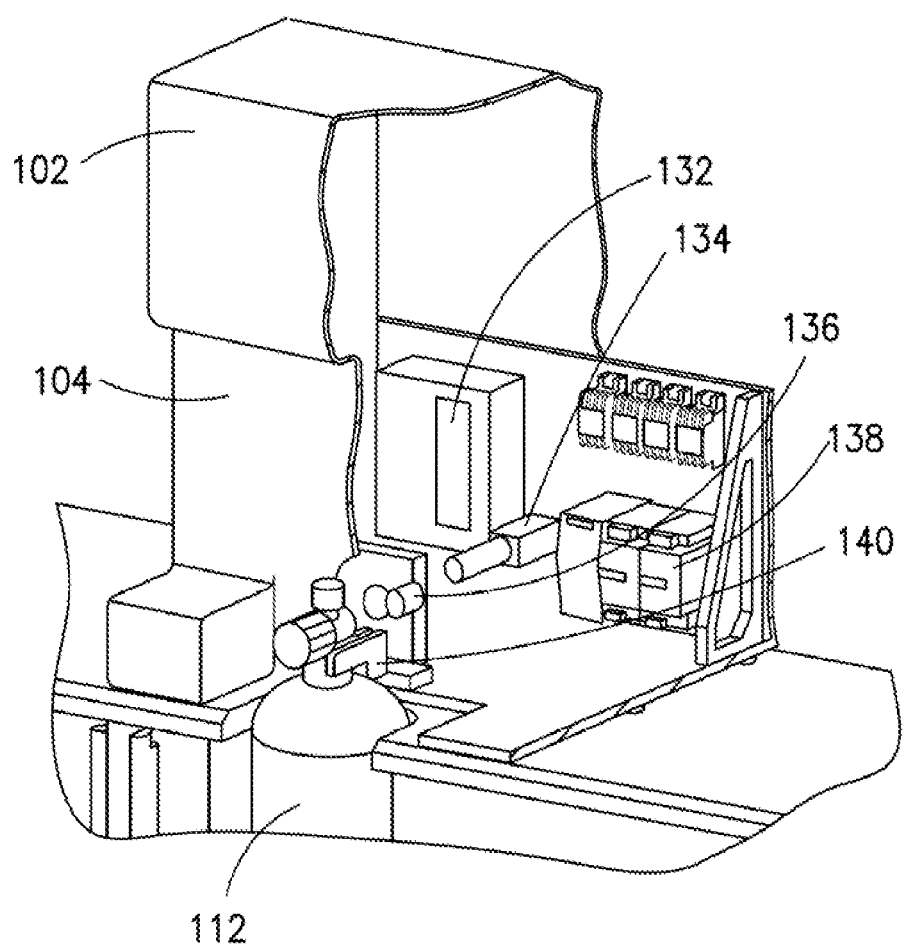
FIG. 3 is a close-up perspective view, partially broken away, of the inspection tool of FIG. 1, showing the details of the tool.

FIG. 3 is a close-up perspective view, partially broken away, of the inspection tool of FIG. 1, showing the details of the tool. The inspection assembly 102 in FIG. 3 illustrates the housing 104 partially broken away to show the optical and electronic components in the housing, with the fluid package 112 positioned for quality assurance determination. The components of the inspection assembly include a central processing unit 132 operatively linked with a power supply 138, a light source 136, and camera/lens assembly 134, with the valve assembly of fluid package 112 being positioned for quality assurance determination by fixture 140, so that the valve nozzle is aligned with the light source and camera/lens assembly.

The light source 136 is adapted to provide a low angled diffuse light for impingement on the valve structure so that the camera/lens assembly 134 can record an image of the valve structure providing quality assurance differentiability of the valve structure in relation to one or more standard or baseline images, to determine whether the valve structure satisfies acceptance criteria or fails such criteria. For this purpose, standard or baseline images are stored in a database or other electronic storage medium in the central processing unit 132, and images recorded by the camera/lens assembly under selected lighting conditions provided by the light source are transmitted from the camera to the central processing unit for image comparison with the standard or baseline images for the fluid packages and valve head assemblies being subjected to quality assurance determination.

The light source may be of any suitable type, and may include an incandescent light source, an LED light source, an infrared radiation source, or other illumination device producing output that is impinged on the valve structure to produce an illuminated image detectable by the camera/lens assembly 134. The camera/lens assembly is arranged to transmit the detected image to the central processing unit 132 for image processing in comparison against the standard or baseline images, to determine whether the valve structure being subjected to quality assurance determination satisfies or fails the acceptance criteria for the valve structure. The central processing unit 132 may be arranged to process the image signals from camera/lens assembly 134 in any appropriate manner.

For example, the image data from the valve structure may be constituted as an autocorrelation function that then is Fourier transformed to yield an illumination power spectrum for digital comparison to baseline or standard spectra for acceptable valve structure, so that the central processing unit outputs the quality assurance determination, e.g., as a visual output to the display screen 114 (see FIGS. 1 and 2). The visual output can for example comprise a colorimetric output, with a green color indication depicting satisfaction of the quality assurance criteria, a yellow color indication depicting borderline satisfaction of the quality assurance criteria, and a red color indication depicting failure of the quality assurance criteria.

The central processing unit may comprise a processor to mitigating with a memory via an address/data bus, wherein the processor can include any commercially available or custom microprocessor, and wherein the memory contains the software instructions and data utilized to implement the functionality of the central processing unit. The memory can include, without limitation, cache, ROM, PROM, EPROM, EEPROM, flash memory, SRAM, and DRAM. The memory may include various categories of software and data used in the central processing unit, including the operating system, application programs, input/output device drivers, and data, e.g., including a database of acceptable valve structures, in the form of spectral data, image profiles, or other image data.

The central processing unit comprises a non-transitory computer readable medium storing machine executable instructions, which when executed by a processor, perform a quality assurance determination for the valve structure being assessed in the quality assurance operation, e.g., to accept or reject the valve structure being assessed, in relation to a predetermined standard or other acceptance criteria. As used herein, the term "criteria" is intended to be broadly construed to encompass a single criterion, as well as multiple quality assurance conditions, values, or characteristics.

Figure 4:
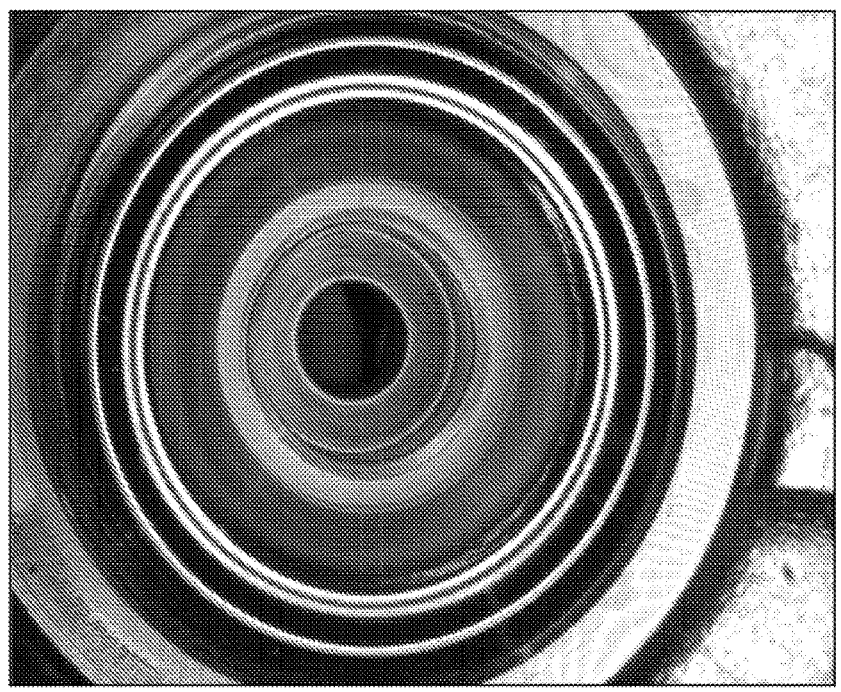
FIG. 4 is a digital image of a valve structure as produced by an optoelectronic inspection system of the present disclosure, showing a dark ring resulting from use of diffuse light and a polished surface, indicating a satisfactory valve structure.

FIG. 4 is a digital image of a valve structure as produced by an optoelectronic inspection system of the present disclosure, showing a dark ring resulting from use of diffuse light and a polished surface, indicating a satisfactory valve structure.

Figure 5:
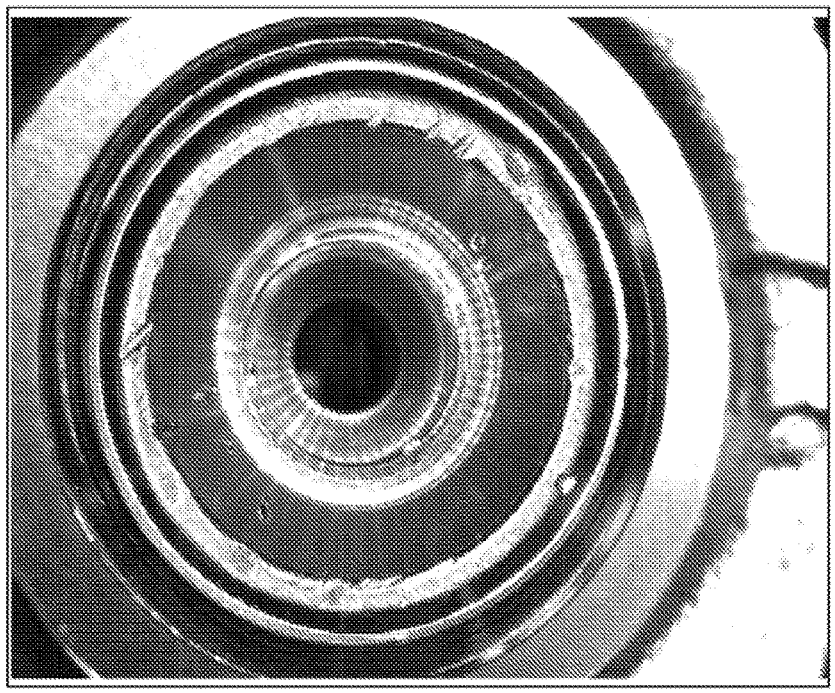
FIG. 5 is a digital image of a valve structure generated by an optoelectronic inspection system of the present disclosure, which in contrast to the valve structure image of FIG. 4 shows a white ring indicative of an unsatisfactory valve structure.

FIG. 5 is a digital image of a valve structure generated by an optoelectronic inspection system of the present disclosure, which in contrast to the valve structure image of FIG. 4 shows a white ring indicative of an unsatisfactory valve structure.

Figure 6:
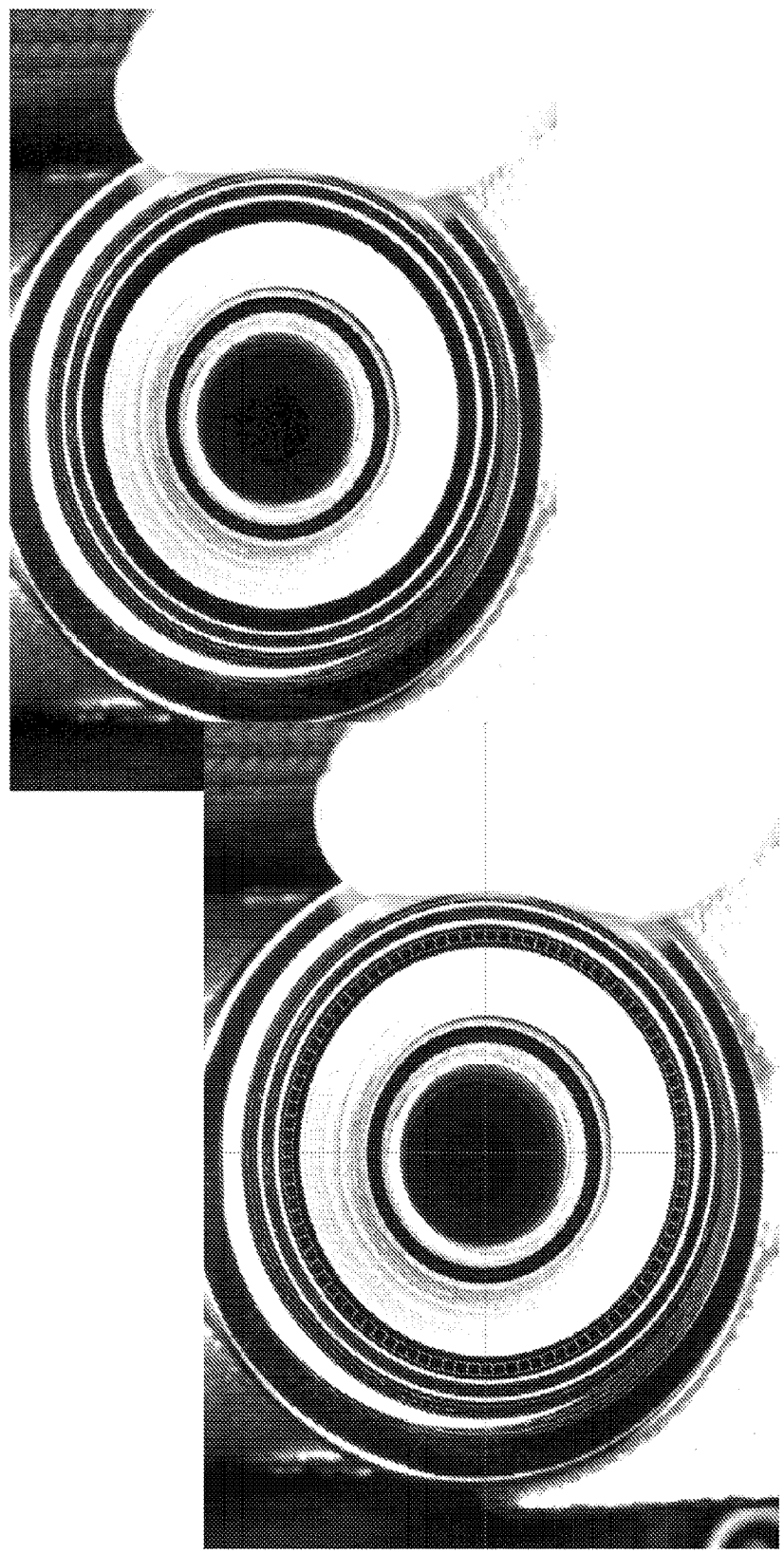
FIG. 6 is a digital image of a 0.500 inch newly manufactured valve structure generated by an optoelectronic inspection system of the present disclosure, in which pristine surface of the valve structure reflects light away from the optics and appears black, indicating acceptable valve structure.

FIG. 6 is a digital image of a 0.500 inch newly manufactured valve structure generated by an optoelectronic inspection system of the present disclosure, in which pristine surface of the valve structure reflects light away from the optics and appears black, indicating acceptable valve structure. The image scanned by the lens/camera assembly is shown on the left-hand side of FIG. 6, showing the individual scan segments, each of which is separately assessed for its character, quality, or condition, as shown by the individual rectangular scan elements superposed on the valve structure, and with the scanned image shown for comparison on the right-hand portion of FIG. 6, without the superposed rectangular scan element array.

Figure 7:
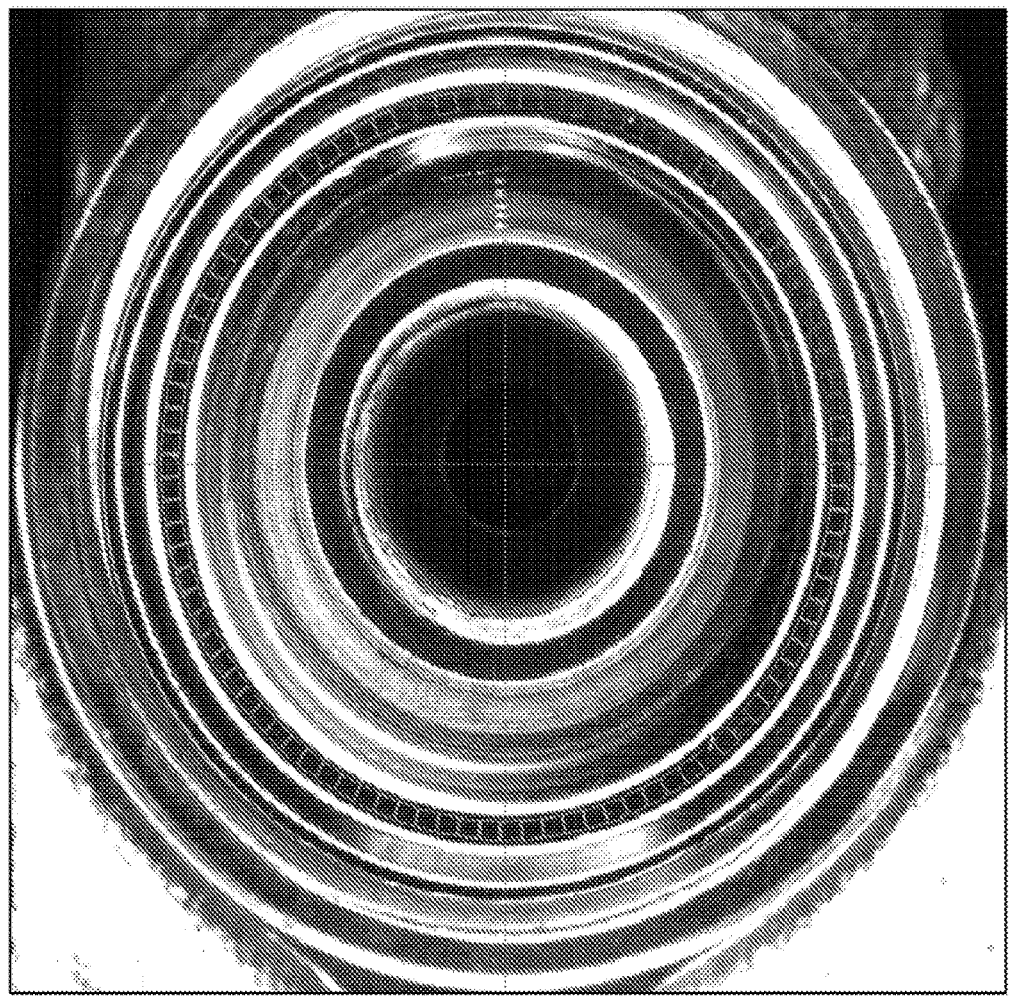
FIG. 7 is a digital image generated by an optoelectronic inspection system of the present disclosure, for a valve structure of a 0.500 inch valve after a period in service in which damaged sealing surface of the valve structure scatters light that is collected by the optics and appears brighter in relation to the digital image of FIG. 6, indicating unacceptable valve structure that however is sufficiently re-workable as to be amenable to reconditioning thereof.

FIG. 7 is a digital image generated by an optoelectronic inspection system of the present disclosure, for a valve structure of a 0.500 inch valve after a period in service in which damaged sealing surface of the valve structure scatters light that is collected by the optics and appears brighter in relation to the digital image of FIG. 6, indicating unacceptable valve structure that however is sufficiently reworkable as to be amenable to reconditioning thereof.

Figure 8:
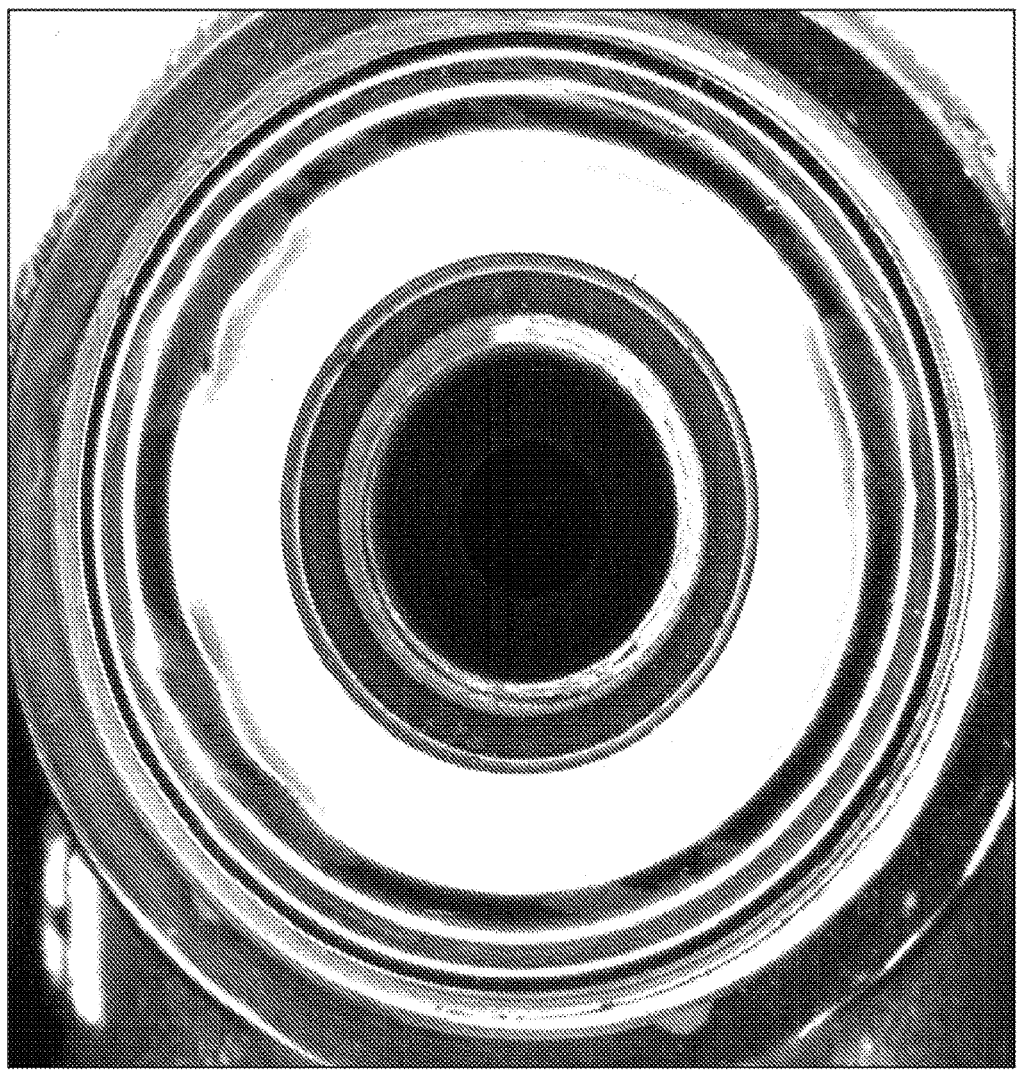
FIG. 8 is a digital image generated by an optoelectronic inspection system of the present disclosure, for a valve structure of a 0.500 inch valve after a period in service in which a significantly damaged sealing surface of the valve structure scatters light that is collected by the optics and appears bright and shiny in relation to the digital images of FIG. 6 and FIG. 7, indicating valve structure that is so extensive as to require scrapping of the valve, as not being amenable to reconditioning of the valve.

FIG. 8 is a digital image generated by an optoelectronic inspection system of the present disclosure, for a valve structure of a 0.500 inch valve after a period in service in which a significantly damaged sealing surface of the valve structure scatters light that is collected by the optics and appears bright and shiny in relation to the digital images of FIG. 6 and FIG. 7, indicating valve structure that is so extensive as to require scrapping of the valve, as not being amenable to reconditioning of the valve.

Figure 9:
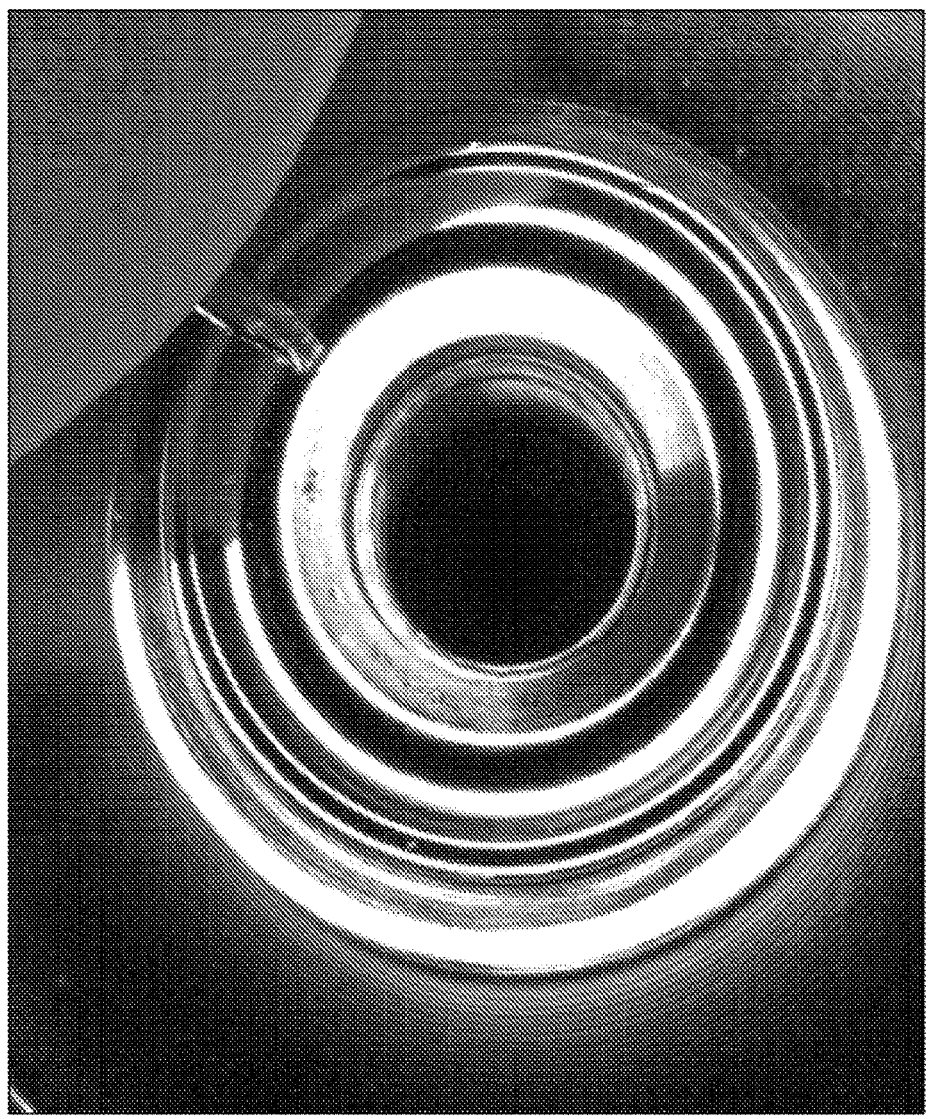
FIG. 9 is a digital image of a 0.250 inch newly manufactured valve structure generated by an optoelectronic inspection system of the present disclosure, in which pristine surface of the valve structure reflects light away from the optics and appears black, indicating acceptable valve structure.

FIG. 9 is a digital image of a 0.250 inch newly manufactured valve structure generated by an optoelectronic inspection system of the present disclosure, in which pristine surface of the valve structure reflects light away from the optics and appears black, indicating acceptable valve structure.

Figure 10:
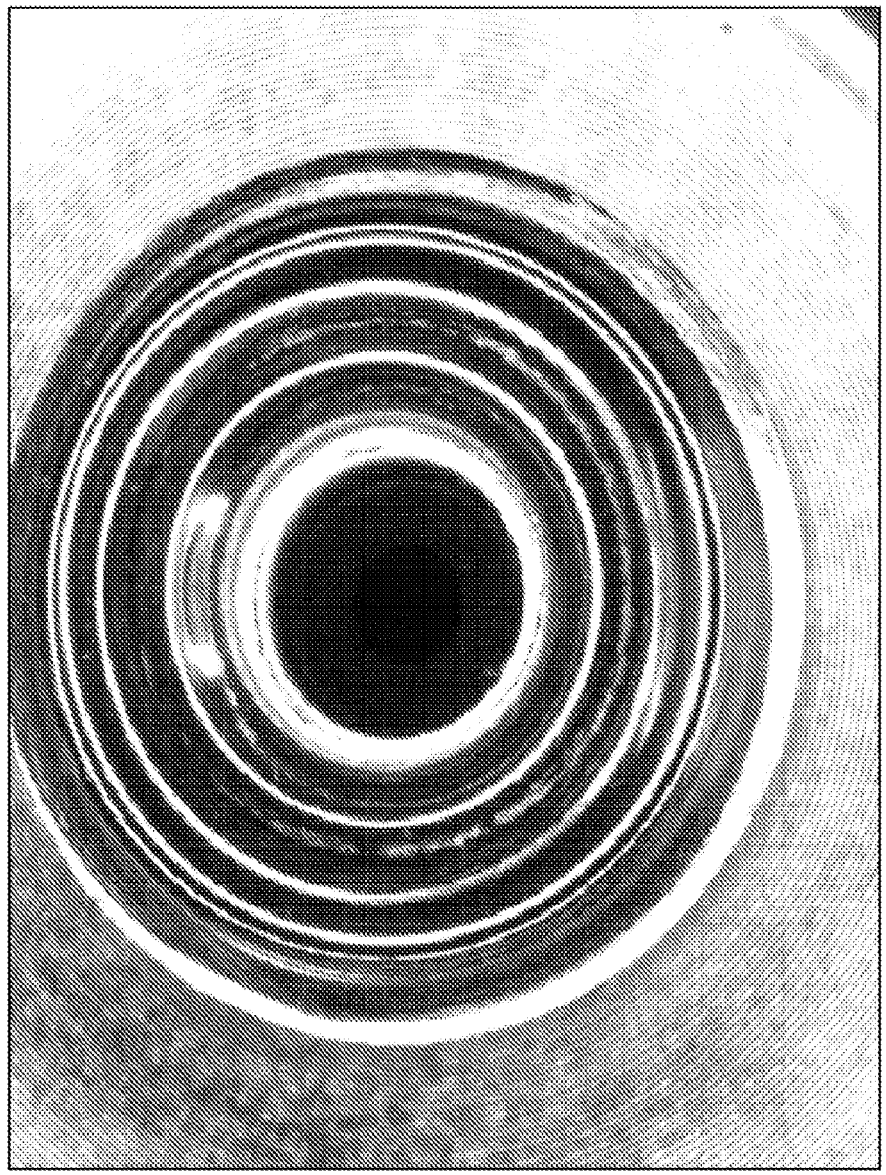
FIG. 10 is a digital image generated by an optoelectronic inspection system of the present disclosure, for a valve structure of a 0.250 inch valve after a period in service in which damaged sealing surface of the valve structure scatters light that is collected by the optics and appears brighter in relation to the digital image of FIG. 6, indicating unacceptable valve structure that however is sufficiently re-workable as to be amenable to reconditioning thereof.

FIG. 10 is a digital image generated by an optoelectronic inspection system of the present disclosure, for a valve structure of a 0.250 inch valve after a period in service in which damaged sealing surface of the valve structure scatters light that is collected by the optics and appears brighter in relation to the digital image of FIG. 6, indicating unacceptable valve structure that however is sufficiently reworkable as to be amenable to reconditioning thereof.

Figure 11:
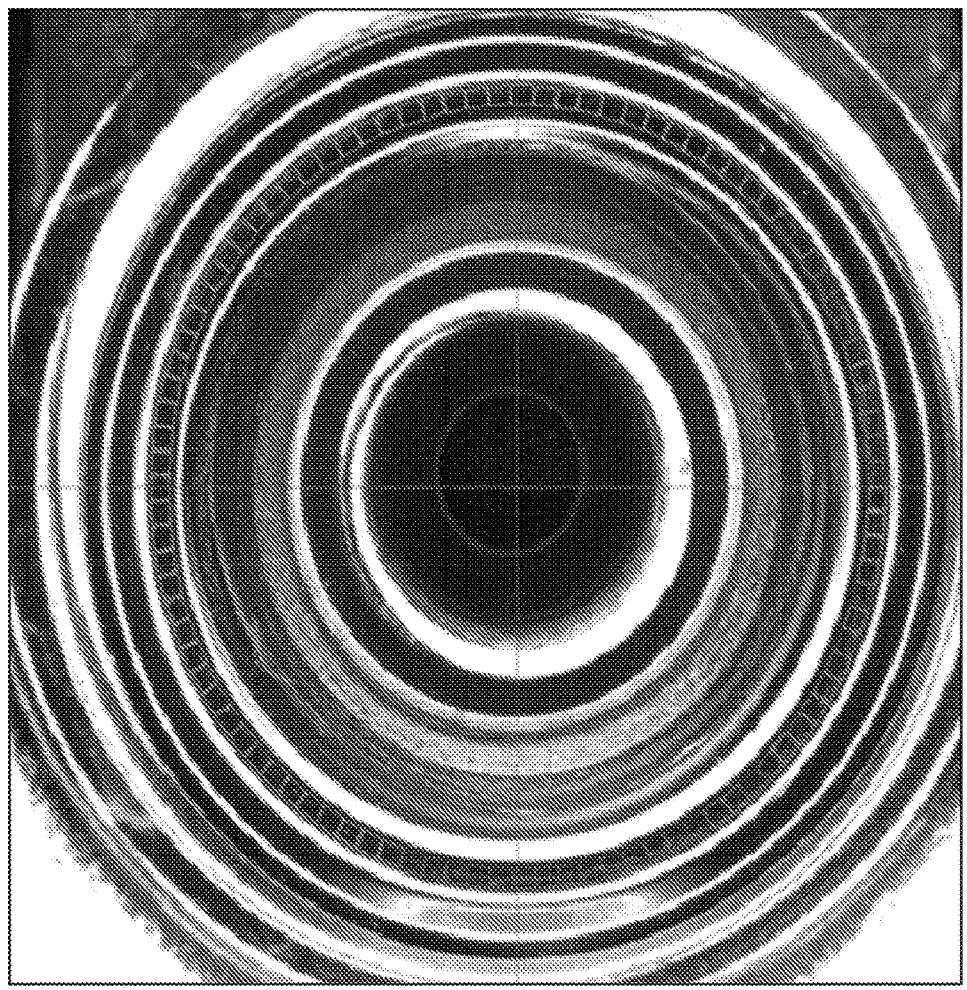
FIG. 11 is a digital image generated by an optoelectronic inspection system of the present disclosure, for a valve structure of a 0.500 inch valve after a period in service in which damaged sealing surface of the valve structure scatters light that is collected by the optics and identifies an unacceptable valve structure that however is sufficiently re-workable as to be amenable to reconditioning thereof
Figure 12:
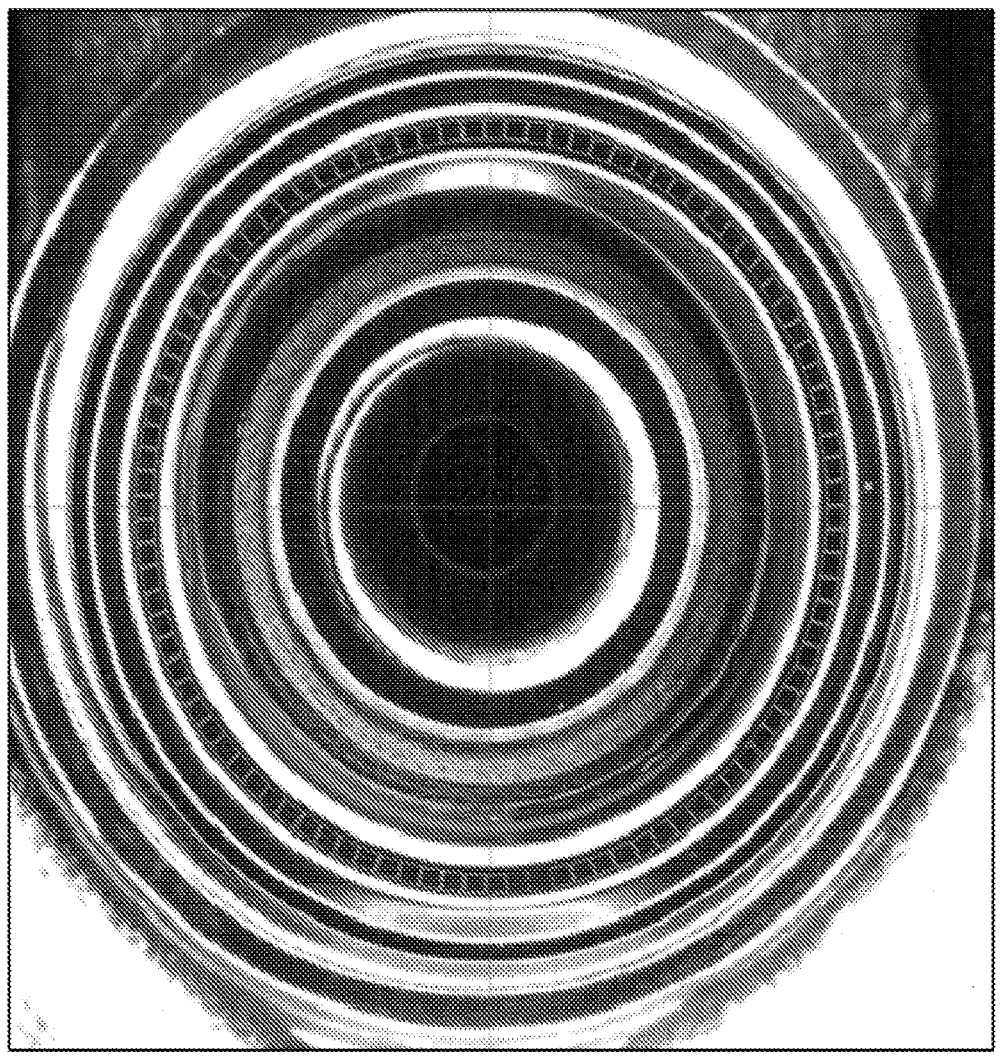
FIG. 12 is a digital image generated by an optoelectronic inspection system of the present disclosure, for the valve structure of FIG. 11 after polishing thereof, showing a detected defect.

FIG. 11 is a digital image generated by an optoelectronic inspection system of the present disclosure, for a valve structure of a 0.500 inch valve after a period in service in which damaged sealing surface of the valve structure scatters light that is collected by the optics and identifies an unacceptable valve structure that however is sufficiently re-workable as to be amenable to reconditioning thereof FIG. 12 is a digital image generated by an optoelectronic inspection system of the present disclosure, for the valve structure of FIG. 11 after polishing thereof, showing a detected defect.

Figure 13:
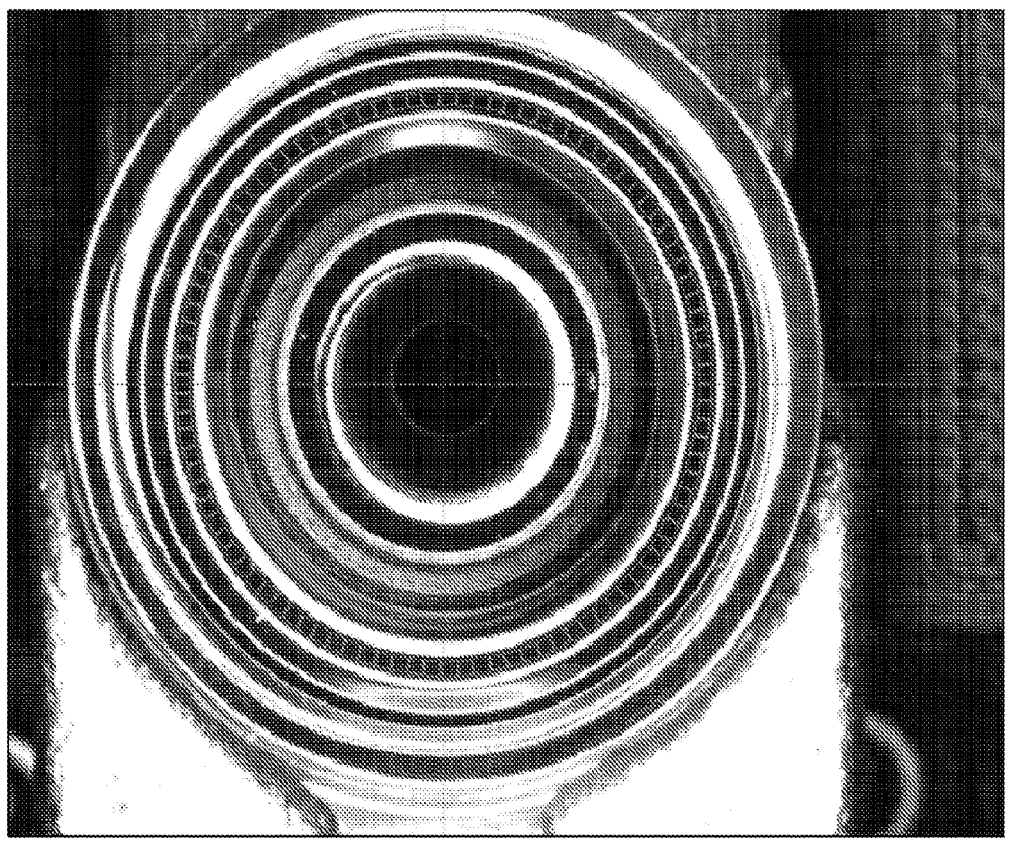
FIG. 13 is a digital image generated by an optoelectronic inspection system of the present disclosure, for the valve structure of FIG. 12 after polishing and wiping thereof with a cellulosic wiping pad.

FIG. 13 is a digital image generated by an optoelectronic inspection system of the present disclosure, for the valve structure of FIG. 12 after polishing and wiping thereof with a cellulosic wiping pad.

Figure 14:
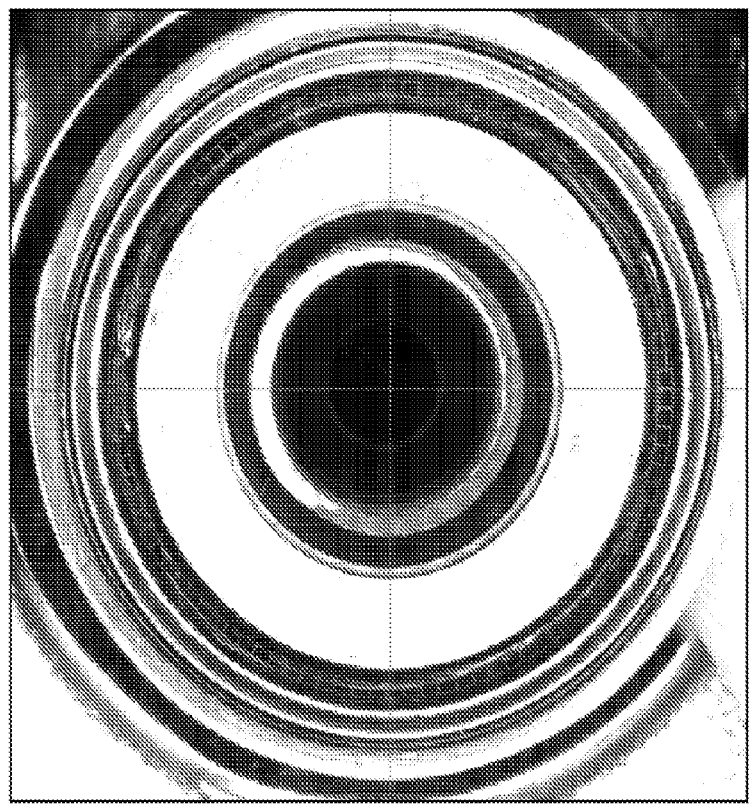
FIG. 14 is a digital image generated by an optoelectronic inspection system of the present disclosure, for the valve structure of a flat valve whose sealing surface has been crushed by over tightening, resulting in a larger outer diameter and a smaller inner diameter, as shown in the enlarged view of FIG. 15.
Figure 15:
FIG. 15 is a digital image generated by an optoelectronic inspection system of the present invention, for the valve structure of FIG. 14.

FIG. 14 is a digital image generated by an optoelectronic inspection system of the present disclosure, for the valve structure of a flat valve whose sealing surface has been crushed by over tightening, resulting in a larger outer diameter and a smaller inner diameter, as shown in the enlarged view of FIG. 15.

Figure 16:
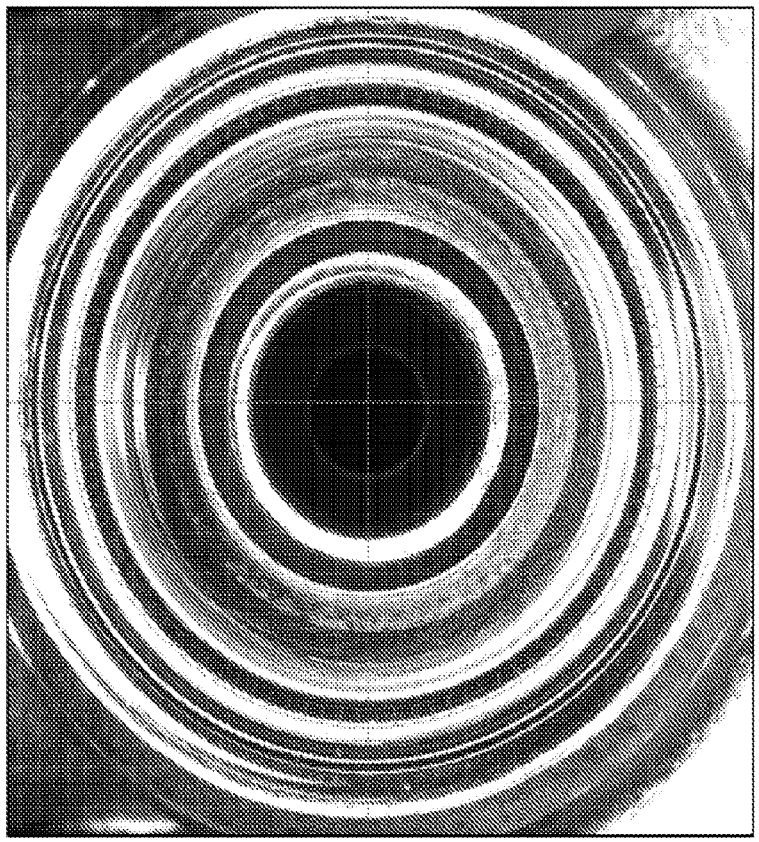
FIG. 16 is a digital image generated by an optoelectronic inspection system of the present disclosure, for a valve structure of an aged valve after extensive service, in which the sealing surface has moved inwardly as the valve has been worn and/or previously polished, as shown by the relative position of the registration elements of the optics system in relation to the sealing surface dark ring, as shown in enlarged scale in FIG. 17.
Figure 17:
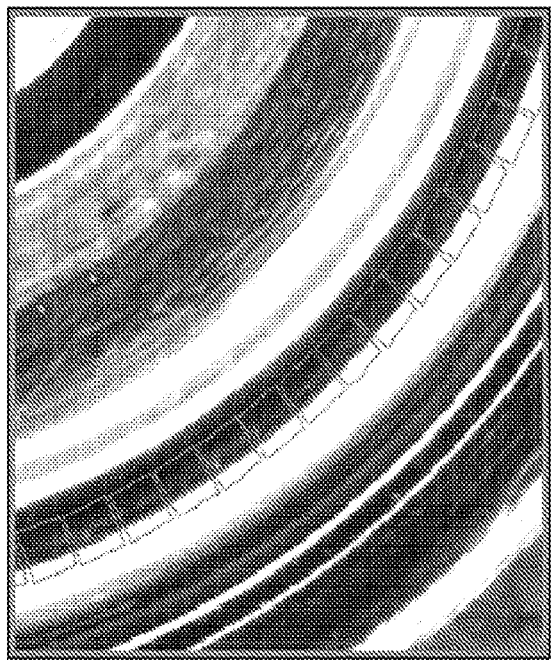
FIG. 17 is a digital image generated by an optoelectronic inspection system of the present invention, for the valve structure of FIG. 16.

FIG. 16 is a digital image generated by an optoelectronic inspection system of the present disclosure, for a valve structure of an aged valve after extensive service, in which the sealing surface has moved inwardly as the valve has been worn and/or previously polished, as shown by the relative position of the registration elements of the optics system in relation to the sealing surface dark ring, as shown in enlarged scale in FIG. 17.

It will be recognized that the optoelectronic inspection system of the present disclosure may be arranged to generate successive images of respective valve structures for pass/fail visual determination of acceptability by the central processing unit in relation to reflectance, scattering, brightness, darkness, and/or other optical characteristics yielded by impingement of the light from the light source on the valve structure undergoing assessment, with such characteristics being evaluated for a multiplicity of pixels or image regions by the central processing unit. In such applications, the image processing algorithms embodied in the software of the central processing unit can be utilized to generate an output, based on average, mean or other representative value(s) in comparison to predetermined acceptance criteria, to provide an operator of the inspection system with a visual representation indicative of a pass/fail determination. The operator of the inspection station can then tag or otherwise identify the accepted or non-accepted status of the fluid supply package and place the fluid supply package in a specific location reflecting its accepted or non-accepted status.

Alternatively, the workstation of the optoelectronic inspection system can be arranged to be fully automated so that respective fluid supply packages are advanced in sequence to the inspection station, placed in position for optical imaging of the valve structure, optically imaged and then automatically transported to an appropriate one of rejected, rework, or accepted package locations, depending on which of such status categories is applicable to a given individual fluid supply package.

It will therefore be recognized that the optoelectronic inspection system of the present disclosure can be widely varied in componentry, layout and operation, to provide a ready and reproducible determination of whether a specific valve structure is acceptable for fluid storage and dispensing operation. Although the inspection system has been described in reference to inspection of valve structures of valves already mounted on vessels of the corresponding fluid supply package, it will be recognized that the valve structure may be inspected prior to securing the valve head assembly to the vessel of the corresponding fluid supply package.

Further, although the present disclosure has been directed to optoelectronic inspection of valve structures of food supply packages, it will be appreciated that the visual inspection system, methodology, and software of the present disclosure is susceptible to implementation for optoelectronic inspection of a wide variety of other structures, materials, etc., as will suggest selves to those of ordinary skill in the art, aced on the disclosure herein.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. An optoelectronic inspection system for determining acceptability of a valve structure, comprising:
    an inspection station adapted to position the valve structure for optoelectronic imaging;
    a light source arranged to impinge light on the valve structure;
    a camera and lens imaging assembly arranged to receive light resulting from interaction of the valve structure and light impinged on the valve structure from the light source, and to responsively generate an optoelectronic imaging output;
    a central processing unit arranged to receive the optoelectronic imaging output from the imaging assembly and to responsively generate an inspection output indicative of whether the valve structure satisfies predetermined acceptability criteria, wherein the central processing unit receiving the optoelectronic imaging output from the imaging assembly constitutes image data of said optoelectronic imaging output as an autocorrelation function that then is Fourier transformed to yield an illumination power spectrum for digital comparison to baseline spectra for acceptable valve structure, and wherein the inspection output comprises a quality assurance determination as a visual output to a display screen.

2. The optoelectronic inspection system of claim 1, wherein the inspection station adapted to position the valve structure for optoelectronic imaging comprises a holder for retaining a fluid supply package including a valve head assembly comprising said valve structure in said position for optoelectronic imaging.

3. The optoelectronic inspection system of claim 1, wherein the light source comprises an illumination device selected from the group consisting of incandescent lamps, light emitting diodes, lasers, ultraviolet lamps, and infrared lamps.

4. The optoelectronic inspection system of claim 1, wherein the central processing unit comprises a processor generating a colorimetric inspection output indicative of whether the valve structure satisfies predetermined acceptability criteria.

5. The optoelectronic inspection system of claim 4, wherein said colorimetric inspection output comprises a green color output when a valve structure satisfies the predetermined acceptability criteria, and comprises a red color output when a valve structure does not satisfy the predetermined acceptability criteria.

6. The optoelectronic inspection system of claim 1, wherein the central processing unit comprises a non-transitory computer readable medium storing machine-executable instructions for determining acceptability of a valve structure.

7. The optoelectronic inspection system of claim 1, wherein the central processing unit comprises a non-transitory computer readable medium storing a database of criteria of acceptable valve structure.

8. The optoelectronic inspection system of claim 1, wherein the central processing unit is adapted to process the optoelectronic imaging output from the imaging assembly for determination of compatibility thereof with said criteria of acceptable valve structure in order to responsively generate the inspection output indicative of whether the valve structure satisfies predetermined acceptability criteria.

9. The optoelectronic inspection system of claim 1, further comprising a transporter apparatus adapted to move a fluid supply package from the inspection station to one of multiple receiving areas dependent on extent of matching by a valve structure thereof to the predetermined acceptability criteria.

10. A method for determining acceptability of a valve structure, comprising:
impinging light from a light source on the valve structure to cause an interaction of the impinged light and the valve structure producing an imaging response;
optoelectronically generating an optoelectronic imaging output based on the imaging response; and
electronically generating, via a central processing unit receiving and processing the optoelectronic imaging output, an inspection output indicative of whether the valve structure satisfies predetermined acceptability criteria,
wherein the central processing unit receiving the optoelectronic imaging output constitutes image data of said optoelectronic imaging output as an autocorrelation function that then is Fourier transformed to yield an illumination power spectrum for digital comparison to baseline spectra for acceptable valve structure, in generating said inspection output, and wherein the inspection output comprises a quality assurance determination as a visual output to a display screen.

11. The method of claim 10, wherein the valve structure is a component of a valve head assembly of a fluid supply package.

12. The method of claim 10, wherein the light source comprises an illumination device selected from the group consisting of incandescent lamps, light emitting diodes, lasers, ultraviolet lamps, and infrared lamps.

13. The method of claim 10, wherein the inspection output comprises a colorimetric inspection output indicative of whether the valve structure satisfies predetermined acceptability criteria.

14. The method of claim 13, wherein said colorimetric inspection output comprises a green color output when a valve structure satisfies the predetermined acceptability criteria, and comprises a red color output when a valve structure does not satisfy the predetermined acceptability criteria.

15. The method of claim 10, wherein the central processing unit comprises a non-transitory computer readable medium storing machine-executable instructions for determining acceptability of a valve structure.

16. The method of claim 10, wherein the central processing unit comprises a non-transitory computer readable medium storing a database of criteria of acceptable valve structure.

17. The method of claim 10, wherein the central processing unit is adapted to process the optoelectronic imaging output for determination of compatibility thereof with said criteria of acceptable valve structure in order to responsively generate the inspection output indicative of whether the valve structure satisfies predetermined acceptability criteria.

18. The method of claim 10, further comprising, after generating the inspection output, mechanically moving a fluid supply package comprising the valve structure to one of multiple receiving areas dependent on extent of matching by a valve structure thereof to the predetermined acceptability criteria.

19. A non-transitory computer readable medium storing machine-executable instructions which when executed carry out a quality assurance determination of a fluid dispensing valve including valve structure on which light has been impinged to produce an imaging response optoelectronically converted to an optoelectronic imaging output, wherein said optoelectronic imaging output is processed according to said machine-executable instructions to generate an inspection output indicative of whether the valve structure satisfies predetermined acceptability criteria, comprising constituting image data of said optoelectronic imaging output as an autocorrelation function that then is Fourier transformed to yield an illumination power spectrum for digital comparison to baseline spectra for acceptable valve structure, in generating said inspection output, and wherein the inspection output comprises a quality assurance determination as a visual output to a display screen.

20. The non-transitory computer readable medium of claim 19, wherein the processing of the optoelectronic imaging output comprises correlation thereof with fluid dispensing valve baseline information for a valve of a type being subjected to the quality assurance determination, from a database of fluid dispensing valve baseline information for multiple valve types.

* * * * *